United States Patent [19]

Franz et al.

[11] Patent Number: 4,544,415
[45] Date of Patent: Oct. 1, 1985

[54] WEATHERING-RESISTANT PEARLESCENT PIGMENTS

[75] Inventors: Klaus-Dieter Franz, Kelkheim; Manfred Kieser; Otto Stahlecker, both of Darmstadt, all of Fed. Rep. of Germany

[73] Assignee: Merck Patent Gesellschaft Mit Beschränkter Haftung, Darmstadt, Fed. Rep. of Germany

[21] Appl. No.: 653,127

[22] Filed: Sep. 21, 1984

[30] Foreign Application Priority Data

Sep. 24, 1983 [DE] Fed. Rep. of Germany ....... 3334598

[51] Int. Cl.⁴ .......................... C09C 3/12; C09D 17/00
[52] U.S. Cl. .............................. 106/288 R; 106/292; 106/308 B; 106/308 Q; 427/214; 428/405; 428/407
[58] Field of Search .................... 106/288, 292, 308 B, 106/308 Q; 427/214; 428/405, 407

[56] References Cited

U.S. PATENT DOCUMENTS

| 3,650,790 | 3/1972 | Klenke et al. ................. 106/308 B |
| 3,711,308 | 1/1973 | Brand et al. .................... 106/308 B |
| 3,867,178 | 2/1975 | Ritter et al. ....................... 427/214 |
| 3,874,890 | 4/1975 | Bernhard et al. ............... 106/308 B |
| 4,084,983 | 4/1978 | Bernhard et al. ............... 106/308 Q |
| 4,086,100 | 4/1978 | Esselborn et al. ................ 106/300 |
| 4,146,403 | 3/1979 | Armanini et al. ............... 106/308 B |
| 4,233,366 | 11/1980 | Sample, Jr. et al. ................ 428/405 |
| 4,456,486 | 6/1984 | Bernhard ........................ 106/308 B |
| 4,457,784 | 7/1984 | Bernhard ........................ 106/308 B |

FOREIGN PATENT DOCUMENTS 1359933 7/1974 United Kingdom .

*Primary Examiner*—Paul Lieberman
*Assistant Examiner*—Willie Thompson
*Attorney, Agent, or Firm*—Millen & White

[57] ABSTRACT

Pearlescent pigments having improved weathering resistance are based on mica flakes coated with metal oxides, these pigments possessing on top of the coat of metal oxide a topcoat which contains a polysiloxane and a rare earth metal compound.

20 Claims, No Drawings

WEATHERING-RESISTANT PEARLESCENT PIGMENTS

BACKGROUND OF THE INVENTION

The invention relates to weathering-resistant pearlescent pigments based on mica flakes coated with metal oxides.

Pearlescent pigments based on mica platelets coated with metal oxides are used in many industrial fields, such as, for example, in cosmetics, namely as pigments for nail varnishes, lipsticks, powders and the like, but also for pigmenting plastics and paints of any kind. However, in particular if these pigments are incorporated into organic polymers, for example if they are used in paints, inks and plastics, it is observed that the weathering resistance of the polymers is impaired by the presence of pearlescent pigment. It is evidently the case that the combined action of natural light, having a high UV content, and of moisture is catalyzed by the metal oxides applied to the mica platelets and causes rapid decomposition of the polymer matrix.

It is known from German Offenlegungsschrift No. 2,215,191 to coat such pigments with an additional coating of methacrylatochromium chloride. This has the effect of achieving good weathering resistance in coating films or plastics. However, if the pigments are coated with effective levels of this chromium complex, the strong green self-color of the additional coating is found to be disadvantageous to the gloss and the coloring quality of the pigment. Moreover, chromium-based coatings are undesirable for various applications, such as, for example, food packaging.

SUMMARY OF THE INVENTION

It is therefore an object of the present invention to provide a chromium-free neutral-color weathering-resistant coating which ideally has no effect on the gloss and the coloring properties of the underlying pigment.

Other objects of this invention will be apparent to those skilled in the art to which this invention pertains.

These objects have been achieved by additionally coating the pigments with a polysiloxane combined with a rare earth metal compound.

The invention accordingly provides pearlescent pigments having improved weathering resistance and being based on mica flakes coated with metal oxides, characterized in that on top of the coat of metal oxide the pigments possess a topcoat which contains a polysiloxane and a rare earth metal compound.

The invention also provides a process for preparing pearlescent pigments having improved weathering resistance and being based on mica flakes coated with metal oxides, characterized in that a mica flake pigment coated with metal oxides is treated at substantially constant pH in aqueous suspension with an aqueous solution of a polysiloxane and an aqueous solution of a rare earth metal salt and in that, thereafter, the pigment is separated off, washed and dried.

The invention also provides for the use of these pigments for preparing weathering resistant formulations containing organic polymers, such as paints, inks and plastics.

DETAILED DISCUSSION

The starting material for the pigments according to the invention can be any conventional mica-based pearlescent pigment. A conventional mica-based pearlescent pigment comprises mica platelets having a diameter of about 1 to 200 μm and a thickness of about 0.1 to 5 μm and having been coated with colored or colorless metal oxides, in particular $TiO_2$, $Fe_2O_3$, $SnO_2$, $Cr_2O_3$, ZnO and other metal oxides, alone or mixed and in a single layer or in successive layers. These pigments are described in numerous patents and patent applications, such as, for example, German Property Rights Nos. 1,467,468, 1,959,198, 2,009,566, 2,106,613, 2,214,545, 2,244,298, 2,313,331, 2,429,762 and 2,522,572, and can be prepared by the processes described there. About 20 to about 60% by weight of these pigments is generally made of mica, and the metal oxides largely account for the remainder.

To apply the additional coating according to the invention, these base pigments are suspended in water to form generally about 5 to about 20% by weight suspensions and are coated with the rare earth metal compound and the siloxane. This additional coating operation can be carried out not only in one step but also in a plurality of steps. The rare earth metal compound and the siloxane are present in separate solutions and can be metered into the pigment suspension either simultaneously or in succession.

The rare earth metal is preferably cerium, which can be used in particular in a 3- or 4-valent state in the form of the sulfate. If the additional coating operation is carried out in two stages, the approximately 5 to 10% by weight cerium sulfate solution is metered into the pigment suspension in the first stage, during which the suspension is held at about pH 5-6 by the simultaneous addition of a base such as, for example, an alkali metal hydroxide solution or ammonia. The cerium is precipitated onto the base pigment in the form of the hydroxide. The amount of solution added is proportioned in such a way that the resulting proportion of rare earth compound in the total pigment is about 0.5 to 3% by weight, calculated on the oxide.

The second coating with the siloxane can then take place. The siloxane is in particular a polyorganosiloxane, especially a polyether-siloxane. These are block copolymers composed of a linear or branched polysiloxane block, for example a polydimethylsiloxane, and one or more polyether or other polar blocks, like e.g. acryl- or methacrylderivatives. Combining the apolar hydrophobic polydimethylsiloxane segments with the polar acryl-, methacryl- or polyether (in particular polyethylene oxide) units as side chains produces copolymers whose properties have been found to be particularly advantageous for treating the pigments according to the invention.

For the purposes of this invention, polysiloxanes, accordingly, are branched block copolymers consisting of polysiloxane segments of the type

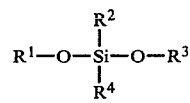

where $R^1$ and $R^3$ are independently each

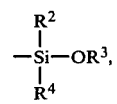

H, $C_{1-4}$-alkyl or polyether and $R^2$ and $R^4$ are each

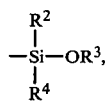

$C_{1-4}$-alkyl, $C_{1-4}$-alkylacrylic ester, $C_{1-4}$-alkylmethacrylic ester or polyether (e.g., poly[$C_{1-4}$-alkylene] ethers). The content of the alkylacrylic or alkylmethacrylic groups in the polysiloxanes can be about 1–10% by weight. The polymers have a viscosity at 25° C. of about 20–20,000 mm². sec⁻¹ and molecular weights of about 500 to 5,000 and, by virtue of the ratio of branched to unbranched alkyl chains in the polyether sequences of for example 50% ethylene oxide to 50% propylene oxide, they are water- and oil-soluble. They are readily precipitated from aqueous solutions by partial hydrolysis as a result of raising the temperature or as a result of adjusting the solution to an acid or strongly alkaline pH. See e.g. Edwin P.Plueddemann: Silane Coupling Agents, Plenum Press, N.Y. 1982.

The siloxane is used in an approximately 1 to approximately 20% by weight aqueous solution or emulsion. The amount of solution to be added to the pigment suspension is proportioned in such a way that the siloxane present in the solution accounts for about 0.5 to 5% by weight of pigment. It must be taken into account that not all of the siloxane is deposited onto the pigment, but that a portion remains in solution. The coated pigment therefore contains about 0.1 to about 5% by weight of siloxane.

Further substances may be deposited onto the pigment together with the siloxane. For instance, the addition of a small amount of alkali metal silicate solu-tion to the siloxane solution or emulsion has been found to be very useful. As a rule, the alkali metal silicate is added in amounts of about 0.05 to about 0.5 g per g of siloxane. It is found, surprisingly, that by this measure in many cases the adhesion of the siloxane to the surface of the pigment can be improved.

In addition to the solution which contains the siloxane and can, if desired, also contain silicate, it is possible to add a further solution of metal salts which are incorporated into the coating in the form of hydroxides. In particular aluminum and zinc have been found to be useful for this purpose, and they are used, individually or together, in amounts of about 0.5 to about 5% by weight, relative to the weight of the total pigment and relative to the oxides. It has been found out, surprisingly, that by addition of these metal salts the resulting pigments in many cases show a reduced tendency to agglomeration and an improved dispersibility.

Unlike the precipitation of the rare earth metal compound, which is carried out at about pH 5–6, the second stage of the additional coating operation is carried out at about pH 6–8, which value is maintained at all times by metering in a base as in the first coating stage.

However, instead of carrying out the additional coating operation in two stages it is also possible to carry out a one-stage additional coating operation. It involves metering solutions of the rare earth metal compound, of the siloxane and, if desired, of an aluminum and/or zinc salt simultaneously into the pigment suspension at about pH 5–6. In none of the additional coating operations is the temperature of the pigment suspension critical in itself, and it can be chosen to be within the temperature range between the freezing point and the boiling point of the suspension. However, as a rule the additional coating operation is carried out at temperatures between room temperature and about 70° C.

When the coating operation has been completed, the mixture is generally stirred for some minutes longer, for example about 10 to 100 minutes longer, and the pigment is then separated off, washed and dried at temperatures of about 80° to 140° C. for a few hours. In the course of the drying, the metal compounds precipitated in the form of hydroxides are dehydrated and will then generally be in the form of oxides or silicates. The pigments according to the invention characteristically have the following contents in the additional coating, each content being expressed as oxide and related to the weight of the finished pigment: rare earth, e.g., cerium: 0.5 to 5% by weight, silicon: 0 to 1% by weight, aluminum: 0 to 3% by weight, zinc: 0 to 3% by weight, siloxane: 0.5 to 5% by weight. The additional coating as a whole should be of the order of about 0.5 to 10% by weight.

When the pigments according to the invention have been dried, they can be used like the known pigments, for example in cosmetics and in plastics, paints and inks. However, because of the improved weathering resistance, preference is given especially to those applications where the pigments are exposed to weathering effects, such as, for example, in automotive paints.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following example(s), all temperatures are set forth uncorrected in degrees Celsius; unless otherwise indicated, all parts and percentages are by weight.

EXAMPLE 1

A suspension in 10 liters of water of 1,000 g of a mica pigment having a silvery interference colors and having been prepared by the process of Example 1 of German Offenlegungsschrift No. 2,522,572 has simultaneously added to it, at 60° C., a solution of 36.5 g of Ce (SO₄)₂ ×4 H₂O in 500 ml of water, a solution of 40 g of Siloxan Tego 281 (a polysiloxane-polyether copolymer from the firm of Goldschmidt AG) and 10 g of sodium silicate in 500 ml of water and a solution of 47.3 g of AlCl₃×6 H₂O in 500 ml of water, while PH 5.5 is maintained by adding 5% sodium hydroxide solution. The mixture is then stirred for an hour, the product is filtered off and washed with 12 liters of water, and the product is filtered off again and dried at 120° C. overnight. The result is a pigment having good gloss and a weathering stability which is markedly improved compared with that of the base pigment.

EXAMPLE 2

A suspension in 10 liters of water of 1,000 g of a mica pigment having a blue interference color and having been prepared by the process of Example 2 of German Offenlegungsschrift No. 2,522,572 has initially added to it, at 60° C., a solution of 25 g of Ce(SO₄)₂×4 H₂O in 500 ml of water, while pH 5.5 is maintained by adding 5% sodium hydroxide solution. After about 20 minutes of stirring, a solution of 40 g of Siloxan Tego 281 and 10 g of sodium silicate in 500 ml of water and a solution of 47 g of $AlCl_3 \times 6\ H_2O$ and 17 g of $ZnCl_2$ in 500 ml of water are added simultaneously, while pH 7.0 is maintained by adding 5% sodium hydroxide solution. After 30 minutes of stirring, the product is filtered off, washed with water and dried at 120° C. overnight. The result is a pigment having good gloss and excellent weathering resistance.

EXAMPLE 3

A suspension in 900 ml of water of 90 g of a mica pigment having a silvery interference color and having been prepared by the process of Example 1 of German Offenlegungsschrift No. 2,522,572 has initially added to it a solution of 2.2 g of $Ce(SO_4)_2 \times 4\ H_2O$ in 100 ml of water, while pH 5.5 is maintained by simultaneously adding 5% sodium hydroxide solution. After 15 minutes of stirring a solution of 2.7 g of Siloxan Tego 281 and 0.8 g of sodium silicate in 150 ml of water and a solution of 3.1 g of $ZnCl_2$ in 150 ml of water are added simultaneously, while pH 7.0 is maintained by adding 5% sodium hydroxide solution. After 60 minutes of stirring the product is filtered off, washed with water and dried at 120° C. overnight. The product is a soft-textured pigment without foreign precipitates which has good gloss and very good weathering resistance.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A pearlescent pigment having improved weathering resistance and comprising mica flakes coated with at least one metal oxide layer, and on top of the metal oxide layer(s), a topcoating comprising amounts of a compatible rare earth metal compound and a polysiloxane of the formula

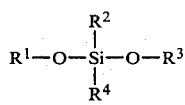

wherein $R^1$ and $R^3$ are independently each

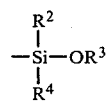

H, $C_{1-4}$-alkyl or poly-$(C_{1-4}$-alkylene) ether, and $R^2$ and $R^4$ are independently each

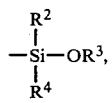

$C_{1-4}$-alkyl, $C_{1-4}$-alkylacrylic ester, $C_{1-4}$-alkylmethacrylic ester or poly-$(C_{1-4}$-alkylene) ether, effective to improve the weathering resistance of the pigment.

2. A pearlescent pigment of claim 1, wherein the rare earth metal compound is cerium oxide or hydroxide.

3. A pearlescent pigment of claim 1, wherein the top layer further comprises a compatible zinc or aluminum compound or both.

4. A pearlescent pigment of claim 1, wherein the top layer further comprises a silicate.

5. A pearlescent pigment of claim 1, wherein the topcoat accounts for about 0.5 to about 10% by weight of the total pigment.

6. A pigment of claim 3, wherein the top layer further comprises a silicate.

7. A pigment of claim 6, wherein the rare earth metal compound is cerium oxide or hydroxide.

8. A pigment of claim 1, wherein the amount of rare earth compound based on the metal is 0.5 to 5% by weight, and of polysiloxane is 0.5 to 5% of weight.

9. A pigment of claim 7, wherein the amount of cerium is 0.5 to 5% by weight; of silicon is 0 to 1% by weight; of aluminum is 0 to 3% of weight; of zinc is 0 to 3% by weight and of polysiloxane is 0.5 to 5% by weight.

10. A pigment of claim 9, wherein the topcoat accounts for about 0.5 to 10% by weight of the total pigment.

11. A process for preparing pearlescent pigments having improved weathering resistance and based on mica flakes coated with at least one metal oxide layer, comprising treating the coated mica flake pigment at a substantially constant pH in aqueous suspension with an aqueous solution of a siloxane and an aqueous solution of a rare earth metal salt whereby the pigment is topcoated with a layer of polysiloxane and of the rare earth compound, and, thereafter, separating the pigment, washing it and drying it.

12. A process of claim 11 wherein the polisiloxane and rare earth compound are coated separately.

13. A process of claim 11, wherein the polysiloxane and rare earth compound are coated simultaneously.

14. A process of claim 11, wherein the rare earth metal salt solution is a solution of a cerium salt.

15. A process of claim 14, wherein the polysiloxane in the topcoating is of the formula

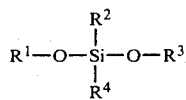

wherein $R^1$ and $R^3$ are independently each

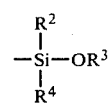

H, $C_{1-4}$-alkyl or poly-$(C_{1-4}$-alkylene) ether, and $R^2$ and $R^4$ are independently each

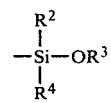

$C_{1-4}$-alkyl, $C_{1-4}$-alkylacrylic ester, $C_{1-4}$-alkylmethacrylic ester or poly-$(C_{1-4}$-alkylene) ether, effective to improve the weathering resistance of the pigment.

16. A process of claim 11, further comprising topcoating the pigments by treating them with a solution containing a zinc or aluminum salt or both, thereby including zinc, aluminum or both in the top coating.

17. A process of claim 11, further comprising topcoating the pigments by treating them with an alkali metal silicate coating solution, thereby including silicate in the top coating.

18. In a formulation of a base ingredient and a pearlescent pigment, the improvement wherein the pearlescent pigment is one of claim 1, whereby the formulation has improved weathering resistance.

19. A formulation of claim 18, wherein the base pigment is an organic polymer.

20. A formulation of claim 18, which is a paint, an ink or a plastic.

* * * * *